(12) United States Patent
Schlenker et al.

(10) Patent No.: US 8,632,495 B2
(45) Date of Patent: Jan. 21, 2014

(54) CONTROL VALVE FOR A MEDICAL SUCTION DEVICE, AND MEDICAL SUCTION DEVICE

(75) Inventors: Stefan Schlenker, Freiburg (DE); Thomas Lietzau, Freiburg (DE); Hartmund Biedermann, Denzlingen (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 53 days.

(21) Appl. No.: 13/364,578

(22) Filed: Feb. 2, 2012

(65) Prior Publication Data
US 2012/0215168 A1      Aug. 23, 2012

(30) Foreign Application Priority Data
Feb. 17, 2011   (DE) .......................... 10 2011 011 398

(51) Int. Cl.
*A61M 39/00*      (2006.01)

(52) U.S. Cl.
USPC ..................................... 604/149; 604/164.02

(58) Field of Classification Search
USPC ........... 604/149, 19, 32, 35, 164.02; 251/298, 251/304, 306, 308
See application file for complete search history.

(56) References Cited

U.S. PATENT DOCUMENTS

| 4,802,506 A | * | 2/1989 | Aslanian ....................... 137/556 |
| 2003/0135151 A1 | * | 7/2003 | Deng .............................. 604/32 |

* cited by examiner

*Primary Examiner* — Nicholas Lucchesi
*Assistant Examiner* — Melissa A Snyder
(74) *Attorney, Agent, or Firm* — Volpe and Koenig, P.C.

(57) ABSTRACT

In a control valve (3) for a medical suction device (1), it is provided that a coupling location (4) of the control valve (3) is includes a guide (8) which, when the control valve (3) is being plugged or fitted into a coupling seat (5) of the medical suction device (1), cooperates with a mating guide piece (9) of the coupling seat (5) for axial guiding and which, in a position turned away from the plugging-in orientation, cooperates with the coupling seat (5) for axially locking the control valve (3) on the coupling seat (5).

19 Claims, 4 Drawing Sheets

CONTROL VALVE FOR A MEDICAL SUCTION DEVICE, AND MEDICAL SUCTION DEVICE

CROSS-REFERENCE TO RELATED APPLICATIONS

This application claims the benefit of German Patent Application No. 10 2011 011 398.3, filed Feb. 17, 2011, which is incorporated herein by reference as if fully set forth.

BACKGROUND

The invention relates to a control valve for a medical suction device, in particular for a bronchoscope, said control valve being designed with a coupling location for a connection, which is rotatable or pivotable about a plugging-in direction, to a corresponding coupling seat of the medical suction device.

The invention further relates to a medical suction device, in particular a bronchoscope, comprising a handle and a control valve releasably connected to the handle, the control valve being designed with a coupling location and the handle being designed, for connection thereto, with a corresponding coupling seat, said control valve being arranged in the coupling seat in such a way that it can be removed therefrom in a rotatable or pivotable manner about a plugging-in direction.

It has become customary for control valves of this type, which are used to establish or interrupt a suction stream, to be connected releasably to a suction flange of a suction device.

For this purpose, the previously known suction devices have a coupling location and a corresponding coupling seat, which together form a latching connection.

Although this latching connection permits a rotatable or pivotable connection in the latched position, there is however the danger of the connection automatically coming loose in the event of careless handling.

SUMMARY

The object of the invention is to improve the connection of the control valve to the handle of a medical suction device.

In a control valve of the type described at the outset, this object is achieved, according to the invention, in that the coupling location is designed with a guide by which the control valve, while being plugged in, can be guided or is guided in a manner secure against turning or pivoting. An advantage of this is that a rotation or pivot guide can be formed on the coupling seat and cooperates with the guide in such a way that the rotating or pivoting movement is permitted in the plugged-in position of the control valve. By contrast, the guiding in a manner secure against turning or pivoting during the plugging-in procedure ensures that the guide is inserted into the coupling seat in one orientation of the control valve and, in an orientation offset from the latter orientation, is locked in the axial direction. In the inserted position in the coupling seat, the guide can be designed to guide the turning or pivoting movement.

For example, it can be provided that the guide is designed as a guide projection on a main body that is rotationally symmetrical about the plugging-in direction. In this case, it can be provided that, in the inserted position of the control valve, the guide engages behind a locking projection on the rotation or pivot guide.

It can also be provided that the guide is formed as a guide projection on a main body having at least one round cross section. Preferably, the main body at least in part describes a cylinder shape. In one embodiment of the invention, it can be provided that the guide is formed within a limited circumferential region. An advantage of this is that the guiding in a manner secure against turning or pivoting during the plugging-in procedure can be easily achieved.

For a simple axial securing of the control valve in the inserted and turned position in the coupling seat, it can be provided that the guide is formed within a limited axial region. An advantage of this is that the axial limit can be used for axially locking the control valve in the inserted and turned position. To obtain a form-fit connection, it can be provided that the guide forms, in the axial direction and/or in the circumferential direction, a change in cross section. In the case where the guide is designed as a guide projection, this change in cross section can be an increase in cross section relative to a main body.

To avoid as far as possible a situation where the control valve can turn accidentally to a release position, it can be provided that a single guide projection is formed on a main body. An advantage of this is that the control valve can be released and removed from the coupling seat only in a single orientation.

In one embodiment of the invention, it can be provided that a radially protruding hose connection is formed. An advantage of this is that the hose connection can be used for turning or pivoting the control valve in the inserted position.

It is particularly expedient if the guide and a or the hose connection are arranged in a common circumferential region. An advantage of this is that the guide can be concealed in the axial direction behind the hose connection.

The terms axial and radial are understood in relation to the rotation axis of the rotating or pivoting movement.

A compact configuration can be achieved if the coupling piece radially surrounds a valve plunger. An advantage of this is that the rotation or pivot axis can be chosen coaxially with respect to the axis of the valve plunger.

In one embodiment of the invention, it can be provided that the coupling location is axially limited by a shoulder. An advantage of this is that an axial abutment is formed as far as which the coupling location of the control valve can be inserted into the coupling seat. Thus, a locking action can easily be achieved in this way by insertion and turning or pivoting.

In an advantageous embodiment, it is provided that a sealing ring is provided on the coupling location, in particular on the free end thereof, which sealing ring protrudes beyond the coupling location in the radial direction. An advantage of this is that a coupling seat receiving the coupling location can be formed with a diameter that is greater than that of the coupling location but smaller than that of the sealing ring. The sealing ring can therefore be used for axially fixing the control valve with a force fit. An advantage of this is that the sealing ring, even in a position in which the guide is axially freed, can axially secure the control valve.

In a medical suction device of the type described at the outset, the object mentioned in the introduction is achieved by the fact that the control valve is designed with a guide and the coupling seat is designed with a mating guide piece that has a shape complementing the guide, wherein the control valve, while being plugged into the coupling seat, is guided by the guide and the mating guide piece in a manner secure against turning or pivoting. The guide and the mating guide piece can be designed, in the inserted position, to guide the turning or pivoting movement. The fact that the connection between coupling location and coupling seat is intended to permit a rotating or pivoting movement in the inserted position automatically ensures that the guide and the mating guide piece axially secure the control valve on the handle in the position when inserted and turned relative to the plugging-in orientation.

For this purpose, it is expedient if the control valve is designed according to the invention.

In one embodiment of the invention, it can be provided that the mating guide piece and the guide are formed at a circumferential position such that a plugging-in of the control valve is permitted with the hose connection aligned parallel to or at an acute angle to a direction of extent of a grip part of the handle. An advantage of this is that the release of the connection between control valve and handle is possible only in an ergonomically unfavorable orientation of the control valve, in which orientation the hose connection interferes with a hand holding the handle by the grip part. Thus it is easily possible to ensure that the control valve does not unintentionally come loose from the handle during use.

To permit the axial locking in the inserted position, it can be provided that a circumferentially extending locking projection is formed on the coupling seat and is interrupted in a circumferential region by the guide. An advantage of this is that the guide can engage behind the locking projection in order to provide the axial securing.

BRIEF DESCRIPTION OF THE DRAWINGS

The invention will now be described in more detail on the basis of an illustrative embodiment, although it is not limited to this illustrative embodiment. Further illustrative embodiments are obtained by combination of one or more features of the claims and/or one or more features of the illustrative embodiment.

In the drawings.

DETAILED DESCRIPTION FO THE PREFERRED EMBODIMENTS

Figure 1:
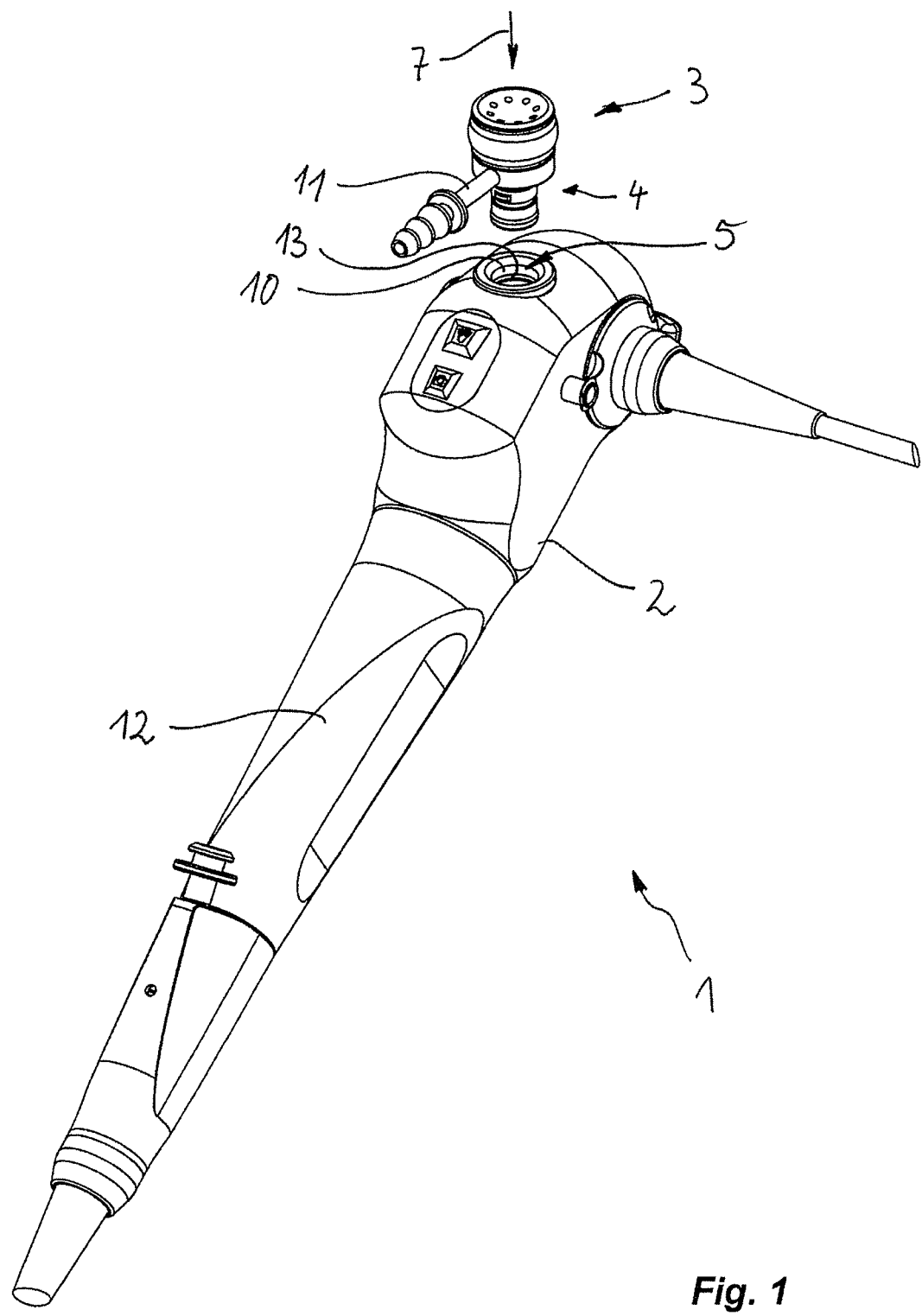
FIG. 1 shows a three-dimensional perspective view of a medical suction device according to the invention with a control valve according to the invention.
Figure 2:
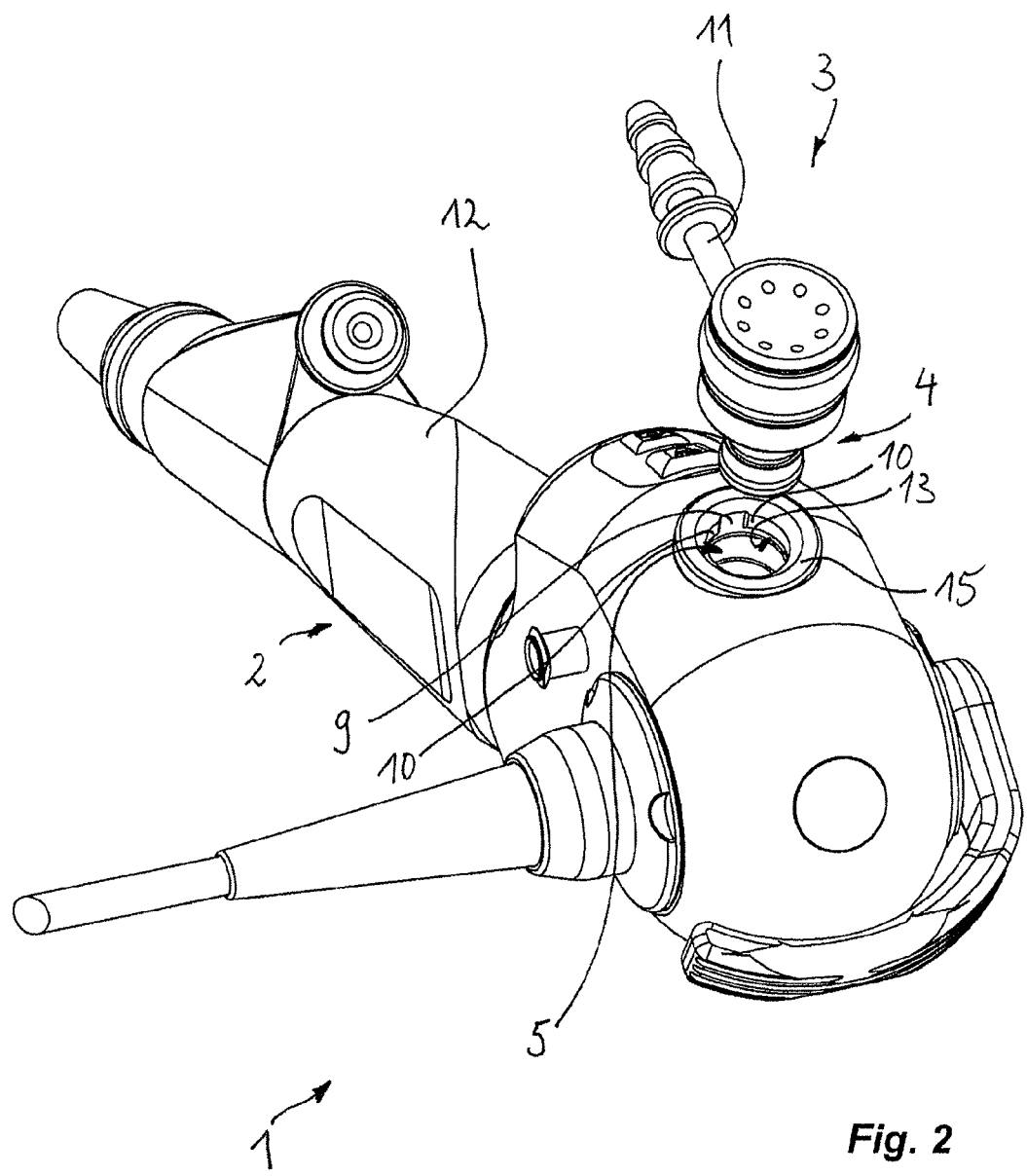
FIG. 2 shows another three-dimensional perspective view of the medical suction device with control valve from FIG. 1.
Figure 3:
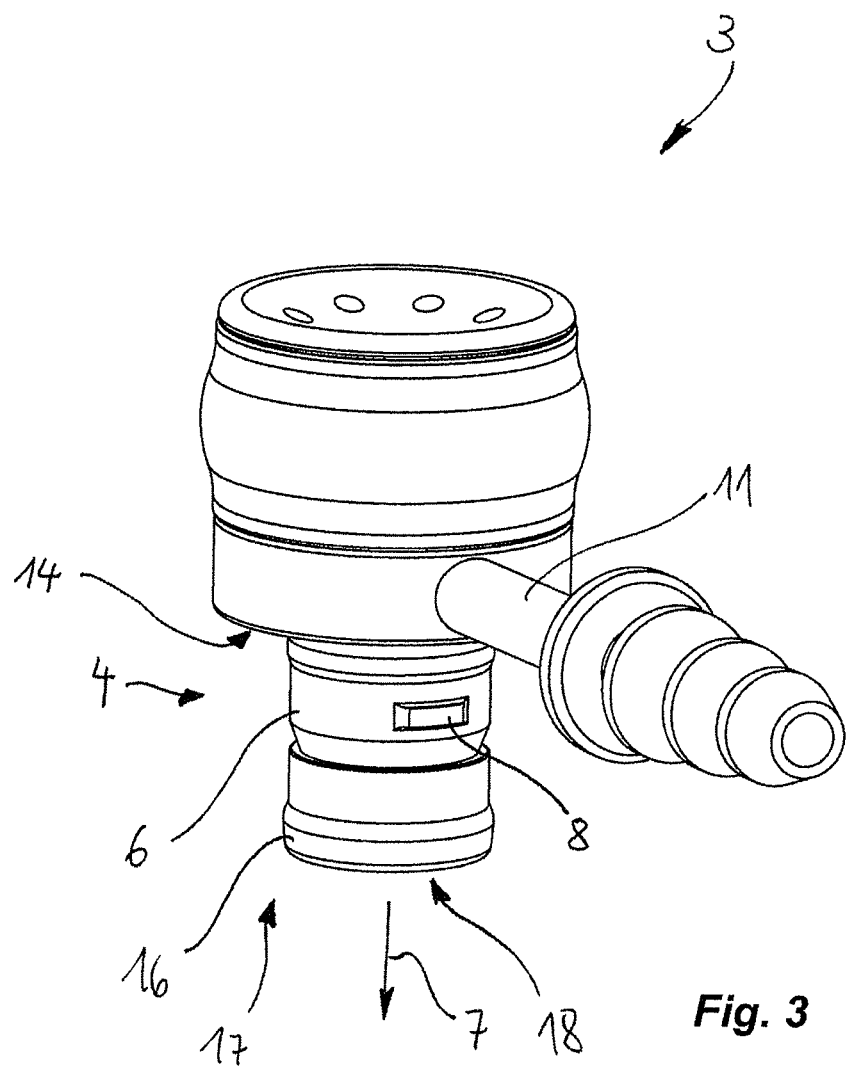
FIG. 3 shows the control valve according to the invention from FIG. 1 in a three-dimensional perspective view from the side.
Figure 4:
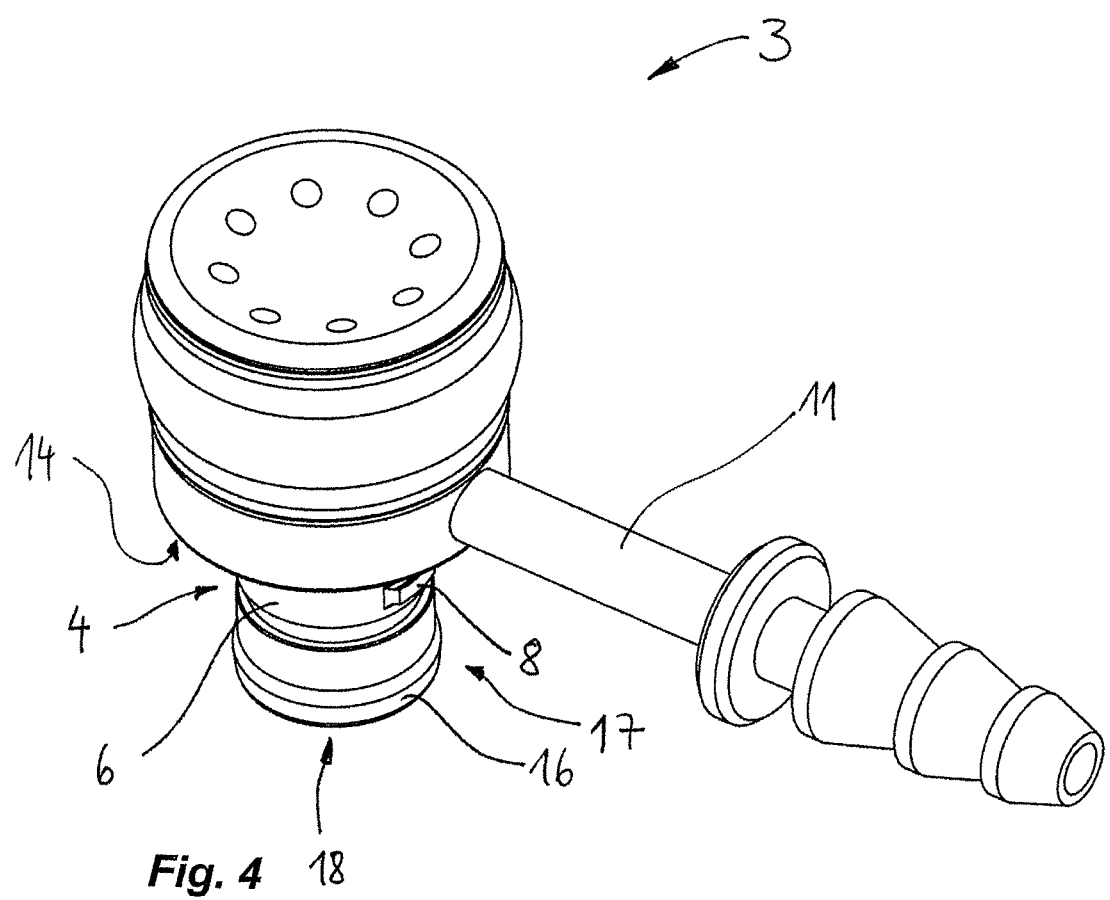
FIG. 4 shows the control valve from FIG. 3 in a three-dimensional perspective view from above.

A medical suction device, designated as a whole by reference number 1 in FIG. 1 and FIG. 2, has a handle 2, which can be connected releasably to a control valve 3.

In the illustrative embodiment, the medical suction device 1 is designed as a bronchoscope.

FIG. 1 and FIG. 2 show the control valve 3 in the released and removed position.

For connection to the handle 2, the control valve 3 is inserted with a coupling location 4 into a corresponding coupling seat 5.

The coupling location 4 has a rotationally symmetrical main body 6, which describes a cylinder shape and which permits a rotating or pivoting movement about the plugging-in direction 7.

A guide 8 is formed as a guide projection on the main body 6, which guide projection describes an increase in cross section in the axial direction and in the circumferential direction.

The guide 8 is formed within a limited circumferential region and, during the plugging-in procedure, engages in a mating guide piece 9, which is formed on the coupling seat 5 as a guide groove, with a groove cross section matching the guide 8, and which extends in the axial direction.

Guide 8 and mating guide piece 9 thus engage one within the other during the plugging-in procedure and create a form-fit connection in the circumferential direction and, as a result, guide the control valve 3 in the axial direction in a manner secure against turning or pivoting.

When the control valve 3 has been inserted and is in a position turned away from the plugging-in orientation, the guide 8 engages behind a locking projection 10 extending in the circumferential direction on the coupling seat 5.

The guide 8 and the locking projection 10 thus create a form-fit connection in the axial direction, which locks the control valve 3 axially in the coupling seat 5.

In this position, the guide 8 guides the turning or pivoting movement of the control valve.

By virtue of the fact that the locking projection 10 is interrupted in one circumferential region by the mating guide piece 9, the guide 8 can be brought out from behind the locking projection 10 in a single orientation. In this position, removal of the control valve 3 from the coupling seat 5 is possible.

A single guide 8 is formed on the cylindrical main body 6. Thus, the control valve 3 can be removed from the coupling seat 5 only in a single orientation.

In this position, the hose connection 11, which protrudes radially from the control valve 3, is aligned at an acute angle with respect to a direction of extent of the grip part 12 of the handle 2, as is shown in FIG. 1 and FIG. 2.

Since, during use, the grip part 12 is grasped by a user's hand, it is practically impossible, during use, for the control valve 3 with its hose connection 11 to move unnoticed into the release position, in which the mating guide piece 9 frees the axial securing of the guide 8 by the locking projection 10.

In order to ensure, in the inserted position of the control valve 3 in the coupling seat 5, that the guide 8 can be easily introduced into the rotation or pivot guide 13 formed by the locking projection 10, the coupling location 4 is limited axially by a shoulder 14 which, on insertion, is placed onto an annular support 15.

The support 15, extending in a ring shape round the coupling seat 5, forms a slide bearing for the rotating or pivoting movement of the control valve 3 on the handle 2.

To make it difficult for the control valve 3 to fall out of the coupling seat 5 in the relative position shown in FIG. 1 and FIG. 2 with respect to the handle 2, the sealing ring 16 at the free end 17 of the coupling location 4 is designed with a larger diameter than the main body 6, as a result of which the sealing ring 16 protrudes beyond the main body 6 of the coupling location 4 in the radial direction.

The sealing ring 16, which is provided for sealing a valve seat 18 of the control valve 3, thus wedges in the cylindrical wall of the coupling seat 5, which wall is adapted to the dimensions of the main body 6, and in so doing makes it difficult for the control valve 3 to fall out.

In the control valve 3 for a medical suction device 1, it is provided that a coupling location 4 of the control valve 3 is designed with a guide 8 which, when the control valve 3 is being plugged or fitted into a coupling seat 5 of the medical suction device 1, cooperates with a mating guide piece 9 of the coupling seat 5 for axial guiding and which, in a position turned away from the plugging-in orientation, cooperates with the coupling seat 5 for axially locking the control valve 3 and/or for guiding a turning or pivoting movement on the coupling seat 5.

The invention claimed is:

1. A control valve (3) for a medical suction device (1), the control valve (3) comprising a coupling location (4) for a connection, which is rotatable or pivotable about a plugging-in direction (7), to a corresponding coupling seat (5) of the medical suction device (1), the coupling location (4) includes a guide (8) by which the control valve (3), while being plugged in, can be guided or is guided in a manner secure against turning or pivoting in the axial direction, and the guide (8) forms, in at least one of the axial direction or a circumferential direction, a change in cross section.

2. The control valve (3) as claimed in claim 1, wherein the guide comprises a guide projection.

3. The control valve (3) as claimed in claim 1, wherein the guide (8) is formed on a main body (6) of the control valve (3) that is at least one of rotationally symmetrical about the plugging-in direction (7), has at least one round cross section, or has a cylindrical shape.

4. The control valve (3) as claimed in claim 1, wherein the guide (8) is formed within at least one of a limited circumferential region, or a limited axial region.

5. The control valve (3) as claimed in claim 2, wherein the guide projection is a single guide projection that is formed on a main body (6) of the control valve (3).

6. The control valve (3) as claimed in claim 1, further comprising a radially protruding hose connection (11).

7. The control valve (3) as claimed in claim 6, wherein the guide (8) and the hose connection (11) are arranged in a common circumferential region.

8. The control valve (3) as claimed in claim 1, wherein the coupling location (4) is axially limited by a shoulder (14).

9. The control valve (3) as claimed in claim 1, wherein a sealing ring (16) is provided on the coupling location (4) on a free end (17) thereof, and the sealing ring (16) protrudes beyond the coupling location (4) in a radial direction.

10. A control valve (3) for a medical suction device (1), the control valve (3) comprising a coupling location (4) for a connection, which is rotatable or pivotable about a plugging-in direction (7), to a corresponding coupling seat (5) of the medical suction device (1), the coupling location (4) includes a guide (8) by which the control valve (3), while being plugged in, can be guided or is guided in a manner secure against turning or pivoting, and the coupling location (4) radially surrounds a valve plunger.

11. A medical suction device (1), comprising a handle (2) and a control valve (3) releasably connected to the handle (2), the control valve (3) including a coupling location (4) and the handle (2) is adapted for connection thereto, with a corresponding coupling seat (5), the control valve (3) is arranged in the coupling seat (5) in such a way that the control valve (3) can be removed therefrom in a rotatable or pivotable manner about a plugging-in direction (7), wherein the control valve (3) includes a guide (8) and the coupling seat (5) has a mating guide piece (9) that has a shape complementing the guide (8), and the control valve (3), while being plugged into the coupling seat (5), is guided by the guide (8) and the mating guide piece (9) in a manner secure against turning or pivoting in the axial direction.

12. The medical suction device (1) as claimed in claim 11, wherein the guide (8) is formed on a main body (6) of the control valve (3) that is at least one of rotationally symmetrical about the plugging-in direction (7), has at least one round cross section, or has a cylindrical shape.

13. The medical suction device (1) as claimed in claim 11, wherein the guide (8) is formed within at least one of a limited circumferential region, or a limited axial region.

14. The medical suction device (1) as claimed in claim 11, wherein a guide projection is formed on a main body (6) of the control valve (3).

15. The medical suction device (1) as claimed in claim 11, wherein the control valve (3) further comprises a radially protruding hose connection (11).

16. The medical suction device (1) as claimed in claim 15, wherein the guide (8) and the hose connection (11) are arranged in a common circumferential region.

17. The medical suction device (1) as claimed in claim 11, wherein the coupling location (4) is axially limited by a shoulder (14).

18. The medical suction device (1) as claimed in claim 11, wherein the mating guide piece (9) and the guide (8) are formed at a circumferential position such that a plugging-in of the control valve (3) is permitted with the hose connection (11) aligned with respect to a direction of extent of a grip part (12) of the handle (2).

19. The medical suction device (1) as claimed in claim 11, wherein a circumferentially extending locking projection (10) is formed on the coupling seat (5) and is interrupted in a circumferential region by the mating guide piece (9).

* * * * *